United States Patent [19]

Schilowitz et al.

[11] Patent Number: 5,264,006

[45] Date of Patent: * Nov. 23, 1993

[54] GUERBET ALKYL ETHER MONO AMINES

[75] Inventors: Alan M. Schilowitz, Highland Park, N.J.; James A. Krogh; Anita R. Mokadam, both of Janesville, Wis.; J. Michael Clumpner, Delavan, Wis.; Paul J. Berlowitz, East Windsor, N.J.

[73] Assignee: Exxon Research and Engineering Co., Florham Park, N.J.

[*] Notice: The portion of the term of this patent subsequent to Mar. 10, 2009 has been disclaimed.

[21] Appl. No.: 811,416

[22] Filed: Dec. 20, 1991

Related U.S. Application Data

[63] Continuation-in-part of Ser. No. 496,474, Mar. 20, 1990, Pat. No. 5,094,667.

[51] Int. Cl.$^5$ ............................................. C10L 1/22
[52] U.S. Cl. ....................................... 44/434; 564/504; 564/505
[58] Field of Search ................... 564/504, 505; 44/434

[56] References Cited

U.S. PATENT DOCUMENTS 5,094,667  3/1992  Schilowitz et al. .................. 44/434

Primary Examiner—Jerry D. Johnson
Attorney, Agent, or Firm—John W. Ditsler; James H. Takemoto

[57] ABSTRACT

Distillate fuel compositions containing an alkyl ether mono amine having the formula $$RO[C_4H_8O]_{(9-18)}CH_2CH_2CH_2NH_2$$

where
R is a highly branched alkyl group derived from a Guerbet alcohol containing between 12 and 40 carbon atoms are effective in reducing the formation of intake valve deposits in internal combustion engines.

12 Claims, No Drawings

GUERBET ALKYL ETHER MONO AMINES

This application is a continuation-in-part of U.S. Ser. No. 496,474, filed Mar. 20, 1990 now U.S. Pat. No. 5,094,667.

BACKGROUND OF THE INVENTION

1. Field of the Invention

This invention concerns an alkyl ether mono amine composition derived from a Guerbet alcohol and its use in a distillate fuel to reduce the formation of intake valve deposits in an internal combustion engine.

2. Description of Related Art

The use of alkyl ether mono and polyamines is known. For example, U.S. Pat. No. 3,440,029 discloses a broad class of alkyl ether mono amines and their use as gasoline deicing additives in carbureted vehicles. However, although these alkyl ether mono amines may be effective deicers, many (if not most) of them are ineffective gasoline intake system detergents. Polyamines are also disclosed in U.S. Pat. Nos. 4,247,301; 4,332,595; and 4,604,103.

In addition, European Patent Application 310,875 discloses the use of certain polyether mono amines prepared by the reductive amination of certain alcohols with ammonia or primary aliphatic amines. Similarly, European Patent Applications 181,140 and 180,455 disclose the use of certain polyether tertiary amines.

More recently, European Patent Application 89114198.8, published Feb. 7, 1990, and having Publication No. 0 353 713, discloses the use of certain Guerbet alkyl ether mono amines in gasoline.

However, none of these publications concern the particular alkyl ether mono amines derived from Guerbet alcohols described below nor their use in the fuel of an internal combustion engine.

SUMMARY OF THE INVENTION

This invention concerns a particular class of alkyl ether mono amines and their use in a distillate fuel. More specifically, we have discovered an alkyl ether mono amine derived from a highly branched butoxylated Guerbet alcohol that has the general formula RO[C$_4$H$_8$O]$_x$CH$_2$CH$_2$CH$_2$NH$_2$ wherein:
- R is a highly branched alkyl group derived from a Guerbet alcohol containing between 12 and 40 carbon atoms and
- x is the number of moles of butylene oxide, which may range from 9 to 18.

We have also discovered that a fuel containing a major amount of gasoline and a minor amount of an oil soluble Guerbet alkyl ether mono amine can reduce the formation of intake valve deposits in an internal combustion engine. A fuel containing these amines can also reduce fuel injector deposits in a fuel injected internal combustion engine.

DETAILED DESCRIPTION OF THE INVENTION

The Guerbet reaction was first described in 1899 by M. Guerbet as a method for condensing two small alcohols into a larger branched alcohol, wherein the branch point occurs at the "beta" carbon (see C. R. Acad. Sci. Paris, 128,511;1002). However, many refinements to the original method of preparation have occurred [e.g. Tetrahedron, vol. 23, page 1723, (1967)]. The overall Guerbet reaction can be represented as follows:

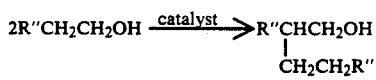

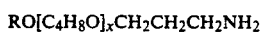

where R" is a hydrocarbyl chain. The product of this reaction is an alcohol with twice the molecular weight of the reactant alcohol minus a mole of water. Much is known about the complex sequence of reactions which comprises the overall reaction shown above. The mechanism is extensively discussed in Tetrahedron, supra. Many catalysts have been described in the literature as being effective for preparing Guerbet alcohols. These catalysts include nickel; lead salts (U.S. Pat. No. 3,119,880); oxides of copper, lead, zinc, chromium, molybdenum, tungsten, and manganese (U.S. Pat. No. 3,558,716); palladium compounds and silver compounds (U.S. Pat. No. 3,864,407).

Guerbet alcohols have unusual properties. These unique properties are partly attributed to their high molecular weight and high level of saturation (A. J. O'lenick Jr. and R. E. Bilbo, Soap/Cosmetics/Chemical Specialties, Apr. 1987, page 52). Unusual properties are also attributed to the so called "beta branch point" (presentation by R. Varadaraj et al., at the American Oil Chemists Society Meeting in Cincinnati, Ohio during May 3-6, 1989). Some of the properties attributed to Guerbet alcohols are low irritation, liquidity to extremely low temperatures, low volatility, relatively reactive and easy to derivitize, useful superfatting agents to re-oil the skin and hair, highly lipophilic, good oxidation stability, and excellent color stability. However, most laboratory studies and commercial applications of Guerbet alcohols and their derivatives have utilized water based systems. Very little, if any, published information is available on their use in hydrocarbon based applications such as gasoline or distillate fuels.

The Guerbet alkyl ether mono amines of this invention are oil soluble and have the general formula:

ti RO[C$_4$H$_8$O]$_x$CH$_2$CH$_2$CH$_2$NH$_2$ wherein:
- R is a highly branched alkyl group derived from a Guerbet alcohol containing between 12 and 40 carbon atoms. By "highly branched" is meant that R contains at least four methyl groups.
- x is the number of moles of butylene oxide, which may range from 9 to 18, preferably from 9 to 15.

More specifically, R has the general formula R$_1$R$_2$CHCH$_2$—wherein R$_1$ contains from 6 to 20 (preferably from 8 to 15) carbon atoms and R$_2$ contains from 4 to 18 (preferably from 6 to 13) carbon atoms. In the most preferred embodiment, R is a Guerbet derived, highly branched alkyl group containing 20 carbon atoms wherein x ranges from 9 to 15.

The ether part of the Guerbet ether amines of this invention is derived from 9 to 18 moles, more preferably from 9 to 15 moles, of butylene oxide. In general, the molecular weight of the Guerbet ether amines will not be monodisperse. The process used for adding butylene oxide will generally result in a distribution of moles of butylene oxide centered around the average x, which may or may not be an integer.

The distillate fuel composition of this invention will, in general, comprise a major amount of gasoline and a minor amount of the highly branched Guerbet ether mono amines described above. However, the precise amount of Guerbet ether amine can vary broadly. As such, only an amount effective or sufficient to reduce the formation of intake valve deposits or fuel injector deposits need be used. Typically, however, the amount of Guerbet ether amine used will range from about 50 to about 2000 ppm, although greater amounts could be used. Preferably, from about 50 to 1000, more preferably from about 100 to about 500, ppm of Guerbet ether amine will be present in the fuel.

The Guerbet alkyl ether mono amines of this invention may be readily prepared by methods known in the art. They may most conveniently be prepared by reaction of the Guerbet alcohol with butylene oxide using a base catalyst at a temperature of 250° to 375° F. Therelative concentration of Guerbet alcohol to butylene oxide will depend on the final product desired. The resulting Guerbet ether alcohol can then be reacted with acrylonitrile, in the presence of alkali at 40° to 135° F., to produce the Guerbet ether nitrile. This reaction is usually carried out with equal moles of the Guerbet ether alcohol and acrylonitrile, although a small excess of acrylonitrile can be used to increase the degree of reaction. The reaction product is than filtered to remove excess polyacrylonitrile. The Guerbet ether nitrile is then reduced in the presence of hydrogen, ammonia, and catalyst, at a temperature of 200° to 350° F., to produce the Guerbet ether mono amine.

Other additives may be included in the fuel. Examples of such additives include antiknock agents (e.g. tetraethyl lead), other detergents or dispersants, demulsifiers, antioxidants, anticorrosives, and the like.

Although the Guerbet alkyl ether mono amines used herein will generally be added to distillate fuel, they may be formulated as a concentrate using a hydrocarbon solvent, an alcohol solvent, or mixtures thereof boiling in the range of about 150° to about 400° F. Preferably, an aromatic hydrocarbon solvent (such as benzene, toluene, xylene, or higher boiling aromatics or aromatic thinners, and the like) is used. Aliphatic alcohols of about 3 to 8 carbon atoms (such as isopropanol, isobutylcarbinol, n-butanol, and the like), alone or in combination with hydrocarbon solvents, can also be used with the Guerbet alkyl ether mono amines. The amount of Guerbet alkyl ether mono amine in the concentrate will ordinarily be at least about 10 wt. % and, generally, will not exceed about 70 wt. %. Similarly, the amount of hydrocarbon solvent will typically range from about 30 to about 90 wt. % of the concentrate.

The distillate fuel composition of this invention (including the fuel concentrate) may also contain a small amount (typically from about 0.02 to about 0.5 wt.% and preferably from about 0.02 to about 0.15 wt. %) of a carrier fluid of low volatility. As used herein, the term "carrier fluid" is meant to include hydrocarbon and oxygenated species. Typically, the carrier fluid will have a kinematic viscosity of between 4 and 75 cSt at 100° C. Examples of such carrier fluids include lubricating oil base stocks, alcohols, polyols, polyol esters, polyalkylene oxides (e.g. Ucon Fluids available from Union Carbide), their mixtures and the like. Sometimes these carrier fluids demonstrate synergistic intake system detergency when used in combination with the Guerbet ether mono amines of this invention.

Although the Guerbet alkyl ether mono amines of this invention are particularly effective intake valve detergents, these amines are also effective in reducing fuel injector deposits in fuel injected internal combustion engines, especially multiport electronically controlled fuel injected engines.

This invention will be further understood by reference to the following Examples, which are not intended to limit the scope of the claims appended hereto.

EXAMPLE 1

Preparation of $C_{20}$ Guerbet Ether Mono Amines

A. Preparation of Poly(oxybutylene)monool of a $C_{20}$ Guerbet alcohol

Exxal 20 (1547 g, 5.2 mols), a $C_{20}$ Guerbet alcohol available from Exxon Chemical Company, and a solution of potassium hydroxide (KOH) in water (45% by weight; 25.2 g, 11.3 g active KOH or 0.20 mol; 0.25 weight %, based on total reactor charge) were introduced into a standard bottom discharge 2 gallon T316 stainless steel Autoclave Engineers' high pressure reactor, equipped with a 600 psi pressure gauge, cooling coils, 1000 psi rupture disc, and a vacuum distillation take-off adapter. While applying a vacuum of 25 to 26 in. Hg to the system, the contents of the reactor were stirred and heated to 112° C. for 2 hours until no residual water was seen to condense on the condensor. The contents were then cooled to ambient temperature (25° C.) by cooling the reactor with cold water several minutes via the cooling coil. 1,2-epoxybutane (2984 g, 41.5 mols or 8 mols of alkylene oxide/mol Exxal 20) was then charged to the reactor through a port opened on the top of the reactor. The port was sealed and the valve leading to the distillation take-off was closed. The mixture was heated to 170° to 175° C. over two hours during which time the pressure rose to 82 psi. The pressure then dropped steadily to 0 psi over 45 minutes as the reaction proceeded. When the pressure reached 0 psi, heating was continued at the same temperature for an additional hour to ensure completion. The contents were then cooled to 120° C., the valve to the distillation take-off opened, and vacuum of 25 to 26 in. Hg applied over a half hour to remove any unreacted butylene oxide. The reaction mixture was then cooled to 90° C. and vacuum filtered hot through a bed of filter aid. 4140.2 g of an amber colored liquid were collected (91.2% of theoretical).

B. Preparation Of $C_{20}$ Guerbet poly(oxybutyl)oxypropanonitrile

The butoxylated alcohol prepared above (3.8 mol) was introduced to a 5 liter 4-neck round bottom flask equipped with a thermometer, overhead stirrer, condensor, and a dropping funnel. A few drops of 45 wt % KOH in water were added to catalyze the reaction. The contents of the flask were heated to 30° C. using a heating mantle with stirring. Acrylonitrile (271.3 g, 5.1 mol) was charged to the dropping funnel and approximately 50 ml aliquots were added in a fast stream over a couple of minutes at about 15 to 20 minute intervals initially over 5 hours in such a manner that maintained the temperature at less than 40° C. After adding 247 g of the acrylonitrile, an additional 4 g of 45 wt % KOH in water was added. The last 24.3 g of acrylonitrile was then added, while monitoring the nitrile and hydroxyl functionality by infrared spectroscopy. The mixture was stirred an additional 1 hour until the infrared spectrum showed no further conversion of hydroxyl functionality. Approximately 70% of the hydroxyl groups had been reacted according to the infrared analysis. 10 ml of water was then added. The mixture was allowed to sit an hour at 40° C. and the water settled. 0.5 N hydrochloric acid was then added dropwise with stirring until the pH of the reaction mixture was neutral (according to pH paper). The neutralized solution was poured through a large filter funnel through #1 Whatman filter paper to remove any acrylonitrile polymer and inorganic salts. 3200 g of the amber colored filtrate (90.8Y. of theoretical) of the ether nitrile was isolated.

C. Preparation Of $C_{20}$ Guerbet poly(oxybutyl)oxypropylamine

Raney Nickel catalyst (40 g, 1.3 wt %, based on ether nitrile) was washed 3 times with 500 ml aliquots of isopropanol. In the first two cases, the solvent was decanted off and fresh solvent added. After suspending the catalyst in the third aliquot of isopropanol, the mixture was added to the 2 gallon Autoclave Engineers' reactor described above. The ether nitrile prepared in B above (3200 g, 3.5 mol) was then added to the reactor and stirring begun. A vacuum of 25 in. Hg was applied to the system by opening the valve of the distillation take-off and the contents of the reactor heated to 120° C. The isopropanol and any residual water was removed by distillation over 2 hours until no condensate was seen forming on the condensor. The distillation valve was closed and the reactor sealed. Hydrogen was then added to a pressure of 10 psi and the reactor vented. The hydrogen purge and venting were repeated. Hydrogen was again added to a pressure of 10 psi and the contents of the reactor cooled over a few minutes to 70° C. by admitting cold water through the cooling coils. Ammonia was added to raise the pressure to 100 psi. Heating was continued and the temperature of the contents increased to 135° C. (pressure had increased to 160 psi) over approximately 30 minutes. Hydrogen was added to maintain the total pressure at 320 psi and the temperature was maintained at 135° to 140° C. for 32 hours. A small sample was taken from a sample port and analyzed for completion of reaction by titrimetric methods and by Infrared Spectrophotometry. The contents of the reactor were cooled to 120° C., vented, and a vacuum of 25 in. Hg applied by opening the distillation valve. The contents were then vacuum distilled for 2 hours to remove residual ammonia. The contents were further cooled to 50° C., then drained from the bottom discharge valve of the reactor, and vacuum filtered warm through a bed of filter aid. In this manner 2950 (91.8% of theoretical) were isolated. An additional 50 to 200 g could be isolated by extraction of the filter aid and catalyst by slurrying in a liter of hexane, followed by refiltration and concentration of product by distillation of the solvent. The yields thus approached 93-98% of theoretical.

EXAMPLE 2

Performance of Highly Branched Guerbet Ether Mono Amines Derived from Butylene Oxide A highly branched $C_{20}$ Guerbet alkyl ether mono amine was synthesized as described in Example 1 from twelve moles of butylene oxide and then blended (at 375 ppm) into a commercial unleaded 93 octane base gasoline. The gasoline also contained small amounts of antirust and antioxidant stabilizers. The fuel was then tested in a BMW 325 for 25 hours on a standard mileage accumulation dynamometer. The base fuel was also tested in the same manner. Following each test, the engines were disassembled, the deposits on the combustion chamber side of the valves were removed, and the intake valves were weighed. The weight obtained was compared to the weight of the valves before the test, with the difference being the total valve deposit weight. The average deposit weight per valve (the sum of the deposit weights divided by the number of valves) is shown in Table 1 below.

TABLE 1

| Run No. | Starting alcohol | moles of butylene oxide | Conc. ppm | mg/valve w/additive |
|---------|------------------|-------------------------|-----------|---------------------|
| A | None | 0 | 0 | 119 |
| B | Exxal 20 | 12 | 375 | 0 |

The data in Table 1 show that effective intake valve deposit control is obtained when using from 9 to 18, and specifically, twelve moles of butylene oxide.

Although this application has been directed to using Guerbet alkyl ether mono amines, the same results would expect to be obtained using polyamines derived from Guerbet alcohols.

What is claimed is:

1. An alkyl ether mono amine having the formula $$RO[C_4H_8]_xCH_2CH_2CH_2NH_2$$

wherein
R is $R_1R_2CHCH_2-$ and contains at least four methyl groups,
$R_1$ is an alkyl group containing from 6 to 20 carbon atoms,
$R_2$ is an alkyl group containing from 4 to 18 carbon atoms, and
x ranges from 9 to 18.

2. The composition of claim 1 wherein x ranges from 9 to 15.

3. The composition of claim 1 wherein $R_1$ contains from 8 to 15 carbon atoms.

4. The composition of claim 3 wherein $R_2$ contains from 6 to 13 carbon atoms.

5. A distillate fuel composition comprising gasoline and the alkyl ether mono amine of claim 1.

6. The composition of claim 5 wherein x ranges from 9 to 15.

7. The composition of claim 5 wherein from about 50 to about 2000 ppm of the alkyl ether mono amine is present in the fuel.

8. A method for reducing the formation of intake valve deposits in an internal combustion engine by operating the engine using a fuel comprising a major amount of gasoline and from about 50 to about 2000 ppm of the alkyl ether mono amine of claim 1.

9. The method of claim 8 wherein the internal combustion engine has fuel injectors.

10. The method of claim 9 further comprising removing at least a portion of the deposits on the fuel injectors.

11. A fuel concentrate comprising
   (a) from about 10 to about 70 wt. % of the alkyl ether mono amine of claim 1, and
   (b) from about 30 to about 90 wt. % of a hydrocarbon solvent, an alcohol solvent, or mixtures thereof which boil in the range of from about 150° to about 400° F.

12. The concentrate of claim 11 wherein the hydrocarbon solvent comprises an aromatic hydrocarbon solvent.

* * * * *